United States Patent [19]

Weaver et al.

[11] Patent Number: 5,250,427

[45] Date of Patent: Oct. 5, 1993

[54] PHOTOCONVERSION OF GASIFIED ORGANIC MATERIALS INTO BIOLOGICALLY-DEGRADABLE PLASTICS

[75] Inventors: Paul F. Weaver; Pin-Ching Maness, both of Golden, Colo.

[73] Assignee: Midwest Research Institute, Kansas City, Mo.

[21] Appl. No.: 904,194

[22] Filed: Jun. 25, 1992

[51] Int. Cl.$^5$ .................. C12N 13/00; C12P 39/00; C12P 3/00; C12P 1/38
[52] U.S. Cl. .................................. 435/42; 435/168; 435/170; 435/244; 435/252.1; 435/801; 435/822; 435/267
[58] Field of Search ............... 435/173, 42, 801, 244, 435/267, 170, 252.1, 168, 822

[56] References Cited

U.S. PATENT DOCUMENTS

| | | | |
|---|---|---|---|
| 1,940,944 | 12/1933 | Fischer et al. | 435/801 |
| 4,467,035 | 8/1984 | Harasawa et al. | 435/801 |
| 4,511,370 | 4/1985 | Hunziker et al. | 435/801 |
| 4,529,701 | 7/1985 | Seely | 435/801 |
| 4,798,801 | 1/1989 | Hitzman | 435/801 |
| 4,919,813 | 4/1990 | Weaver | 435/267 |
| 4,936,996 | 6/1990 | Messing | 435/267 |

Primary Examiner—Herber J. Lilling
Attorney, Agent, or Firm—Ken Richardson

[57] ABSTRACT

A process is described for converting organic materials (such as biomass wastes) into a bioplastic suitable for use as a biodegradable plastic. In a preferred embodiment the process involves thermally gasifying the organic material into primarily carbon monoxide and hydrogen, followed by photosynthetic bacterial assimilation of the gases into cell material. The process is ideally suited for waste recycling and for production of useful biodegradable plastic polymer.

8 Claims, 3 Drawing Sheets

PHOTOCONVERSION OF GASIFIED ORGANIC MATERIALS INTO BIOLOGICALLY-DEGRADABLE PLASTICS

CONTRACTUAL ORIGIN OF THE INVENTION

The U.S. Government has rights in this invention under Contract No. DE-AC02-83CH10093 between the U.S. Department of Energy and the National Renewable Energy Laboratory, a Division of the Midwest Research Institute.

BACKGROUND OF THE INVENTION

1. Field of the Invention

The present invention relates generally to conversion of organic materials into biological plastics. Specifically, the present invention relates to a process for converting dry biomass wastes or inexpensive organic fuels, for example, into bioplastics suitable for use as biodegradable thermoplastics.

2. Description of the Prior Art

Municipal solid waste is similar to other forms of organic wastes (e.g., sewage sludges, manures, and agricultural and forestry residues) in that it is a very biochemically heterogeneous substrate that is only slowly metabolized by interactive, complex mixtures of microbes. High-yield, useful products are, at best, limited to methane. Alternatively, dry low-grade organic materials can be thermally gasified into a fairly homogeneous synthesis gas product, primarily comprised of CO and $H_2$ with smaller amounts of $CO_2$, $CH_4$, $H_2S$, and other trace gases. Chemical energy conversion efficiencies can be as high as 80–85%. Inexpensive organic fuels, such as coal, petroleum, natural gas, peat, and shale, also can be readily thermally gasified to a similar synthesis gas product.

In the past, a few species or mixtures of bacteria have been described that are able to utilize CO and/or $H_2$. However, their inability to utilize light energy necessitates that most of the chemical energy of the substrates is excreted in products such as acetate or $CH_4$. Less than 6% of the substrate is converted into new cell material by the anaerobic metabolism of these microbes. In general, aerobic bacteria commonly convert about 25% of easily digestable substrates into new cell mass. A more complete conversion of synthesis gas substrates into cell mass product would clearly be beneficial.

Depending upon growth conditions, the newly-formed bacterial cell mass can be comprised primarily of protein, carbohydrate, or lipid constituents. Each constituent may have commercial value. Bacteria high in protein content are potentially capable of use as sources of animal feed and human food supplements. Carbohydrate materials derived from bacteria are potentially useful for their rheological properties and as emulsifiers. To date, lipid materials isolated from microbes have been commercially used only in niche markets.

A lipid material, poly-$\beta$-hydroxybutyrate (PHB) is commonly synthesized by a number of different microbes and packaged into compact, 0.2–0.8 micron granules. Hydroxyvaleric acid, if synthesized or supplemented in the growth medium, can also be assimilated into the polymer, as can any other of a number of hydroxylated organic acids. With breakage of the microbial cells, the polymer granules are released. Granules have been determined to be better than 98% PHB or copolymer, the remainder being primarily adsorbed surface protein. The granules contain linear polyester chains with molecular weights up to 500,000 daltons or more. PHB is a high-modulus, natural plastic with a melting point of 170° C. and physical properties similar to polystyrene. When 5% to 20% hydroxyvaleric acid is incorporated into the polymer (PHB-V), the melting point is lowered and the product is stronger and more flexible with properties similar to polypropylene. At 30% hydroxyvalerate, the bioplastic has physical properties similar to polyethylene. Being biological products, both PHB and PHB-V can be completely biodegraded by common microbes indigenous to soil and aquatic environments. These types of biologically-made polymers and copolymers are generically termed bioplastics.

Commercial production of PHB and PHB-V for specialty uses, such as for biodegradable sutures or for time-release drug delivery, is currently limited to a few companies, notably Imperial Chemical Industry, Ltd. (ICI) of England. Processing technology and applications for the polymers are already well established. Much of the technology has been adapted from the single-cell protein industry. Operating costs utilizing ICI's methodology are high due to the existing requirements for sterility and the large amounts of sugar, organic acid, ammonium ion, and other defined nutrients necessary for the development of the types of microbial cell mass that ICI employs. Efficiencies of sugar and organic acid conversion into polymer are 25–30%. A 10,000-ton plant using ICI's technology is estimated to produce PHB-V at $2 per pound, which compares to non-degradable petroplastics at about 60 cents per pound.

There has not heretofore been provided a technique or process for simple and effective conversion of inexpensive, heterogeneous organic materials into biological plastics.

SUMMARY OF THE INVENTION

It is an object of this invention to provide a process for the conversion of organic wastes to hydrogen and carbon monoxide and then conversion to microbial plastic polymer using photosynthetic bacteria.

It is another object of this invention to utilize photosynthetic bacteria in a process for producing bioplastics in an effective and efficient manner.

It is another object of this invention to utilize photosynthetic bacteria and solar energy for producing bioplastics which are suitable for use as biodegradable plastics.

It is another object of this invention to provide a process for converting low-cost organic materials into bacterial cell mass which is high in bioplastic polymer.

It is yet another object of this invention to provide a process for converting synthesis gas into bioplastic in an efficient manner.

Additional objects, advantages, and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

To achieve the foregoing and other objects and in accordance with the purpose of the present invention, as embodied and broadly described herein, the invention may comprise a process for producing bioplastics, wherein the process includes the steps of:

(a) combusting or thermally gasifying organic material to produce a synthesis gas product comprising primarily carbon monoxide and hydrogen;
(b) feeding the gaseous nutrients to photosynthetic bacteria; and
(c) exposing the bacteria to radiant energy, whereby the gaseous nutrients are assimilated into bacterial cell mass which is high in bioplastic.

The process of this invention is useful for rapidly converting low-cost biomass materials, such as lignocellulosics, into bioplastic for use as a biodegradable plastic. The organic materials are thermally gasified to form primarily carbon monoxide and hydrogen products, followed by photosynthetic bacterial assimilation of the gases into cell material, which can be as high as 90% bioplastic. The overall process is nearly quantitative, driven by the energy of sunlight, for example. Photosynthetic bacteria are highly productive, with mass-doubling times as low as 90 minutes, and offer potential as a one or two day crop for bioplastic production.

The nutrients (carbon monoxide and hydrogen) provided by combusting low-cost waste materials are recombined by photosynthetic bacteria into bioplastic product. The process is carried out under anaerobic conditions.

In the present invention, the cost of production of bioplastics is dramatically decreased using photosynthetic bacteria, sunlight, and inexpensive synthesis gas derived from waste organic materials. Further production cost decreases are realized by the apparent absence of requirements for sterile conditions (few other microbes will grow under these conditions) and much higher conversion efficiencies than previously attainable.

Other advantages of the process of the invention will be apparent from the following detailed description.

BRIEF DESCRIPTION OF THE DRAWINGS

The accompanying drawings, which are incorporated into and form a part of the specification, illustrate preferred embodiments of the present invention, and together with the description, serve to explain the principles of the invention.

DETAILED DESCRIPTION OF THE PREFERRED EMBODIMENTS

Figure 1:
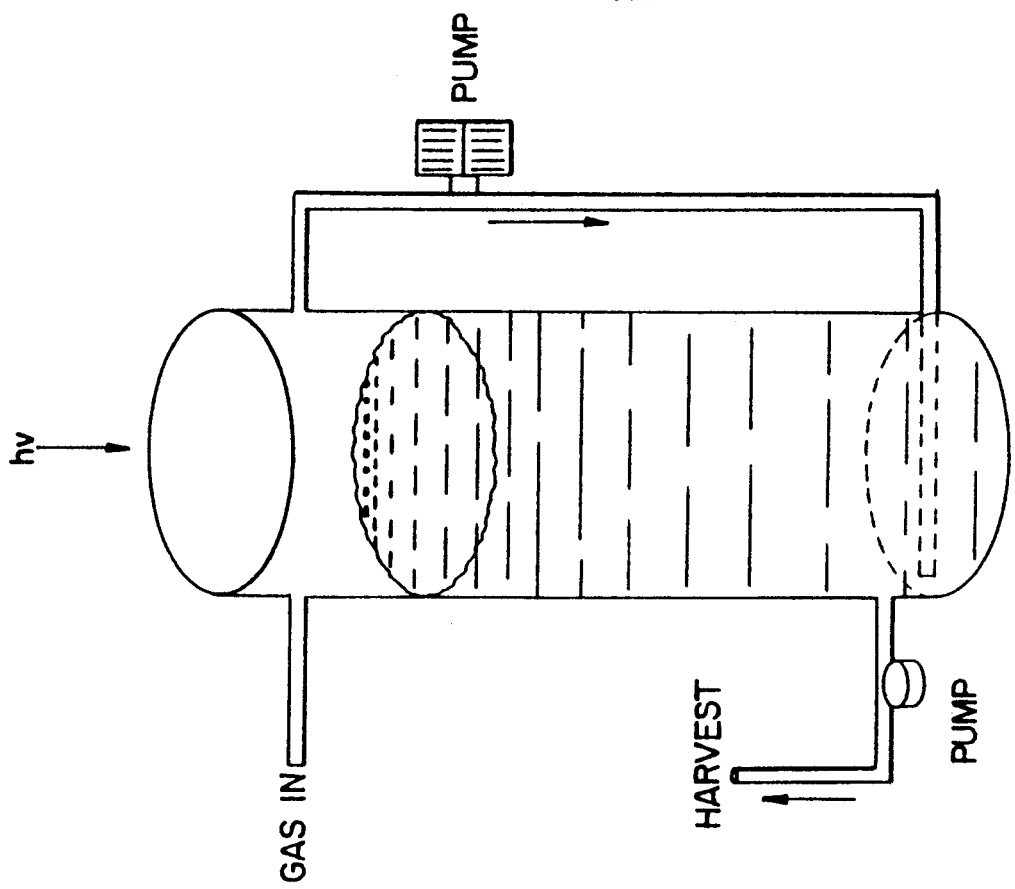
FIG. 1 illustrates one embodiment of reactor which is useful in this invention.

The organic materials which may be converted into bioplastic in accordance with the principles of this invention are carbonaceous materials which are or can be thermally gasified into a synthesis gas, including for example, natural gas, coal, petroleum fractions, shale oil, peat, municipal solid waste, agricultural waste, forestry residues, organic chemical waste, manures, or other forms of biomass. Steam-reformed natural gas also generates similar gaseous products.

The present invention provides techniques for photobiologically converting the gaseous nutrients into bioplastic in a rapid and efficient manner.

Thus, the techniques of the present invention pertain to the conversion of synthesis gas (i.e., hydrogen and carbon monoxide gaseous mixtures) into bioplastic regardless of where the gaseous nutrients come from.

The bacteria capable of using synthesis gas or producer gas for growth are all members of the bacterial order Rhodospirillales of photosynthetic or phototropic bacteria. Not all members of this order are useful in this invention however. The photosynthetic bacteria which are useful in this invention are capable of growing on carbon monoxide. All of the useful bacteria were selected for their ability to grow in light solely on carbon monoxide, hydrogen, nitrogen and mineral salts.

More than 350 strains of photosynthetic bacteria have been isolated from natural soil and water samples through visibly irradiating enrichment cultures growing on carbon monoxide as the sole source of carbon. No particular species of photosynthetic bacteria dominated the isolates. This capacity for growth on carbon monoxide identifies the unique strains of photosynthetic bacteria which are useful in the practice of this invention. The photoconversion of carbon monoxide and hydrogen into new cell material by these bacteria approaches 100%.

Useful strains of photosynthetic bacteria have been characterized within the following genera and species, for example, *Rhodocyclus gelatinosus, Rhodopseudomonas palustris, Rhodospirillum molischianum,* and *Rhodopseudomonas capsulata*. Each of these strains is capable of quantitatively photoconverting gasified organic waste materials into new cell material.

Thermally gasifying organic wastes rapidly converts nearly all of the material into a fairly homogeneous synthesis gas, consisting primarily of CO and $H_2$.

$$(CH_2O)_n \xrightarrow{\text{limiting } O_2} nCO + nH_2 \qquad \text{(Eq. 1)}$$

If limiting air or enriched $O_2 + N_2$ is used for the gasification, a producer gas is formed and the $N_2$ exits in the gas stream unchanged.

$$(CH_2O)_n \xrightarrow{\text{limiting } O_2 + mN_2} nCO + nH_2 + mN_2 \qquad \text{(Eq. 2)}$$

Both CO and $H_2$ can be readily metabolized by a few bacteria, notably strains of photosynthetic bacteria. Nearly all photosynthetic bacterial strains are also able to reduce $N_2$ to the level of ammonia for use in protein synthesis. A few strains of photosynthetic bacteria are able to assimilate CO and $H_2$ while simultaneously reducing $N_2$. These bacteria are able to grow completely autotrophically on producer gas containing $H_2$, CO, and $N_2$. The process is driven by the energy of light.

$$nCO + nH_2 + mN_2 \xrightarrow{h\nu} (CH_2ON_{2m})_n \qquad \text{(Eq. 3)}$$

Experiments indicate that the CO and $H_2$ are totally consumed by the photosynthetic bacteria leaving only excess nitrogen, if present, for disposal. Therefore, the overall reaction may be shown as:

$$(CH_2O)_n + mN_2 \xrightarrow{h\nu} (CH_2ON_{2m})_n \qquad \text{(Eq. 4)}$$

Microbes which have been tested in accordance with this invention perform a water-gas shift reaction on the CO component of synthesis gas or producer gas, yielding additional hydrogen and carbon dioxide. This reaction occurs at equivalent rates in darkness or in light. Starting with gas phases containing 20% CO (all of the photosynthetic microbes isolated tolerate at least this concentration of CO), hydrogen production is stoichiometric with CO consumption. At equilibrium after the shift (ambient temperature and pressure), the hydrogen gas phase concentration is 20% and the CO concentration is less than 18 ppm. The enzymes responsible for the CO shift are highly active. The initial enzyme, CO dehydrogenase, can oxidize CO (to methyl viologen) at rates of 5 moles/ hr·mg enzyme (assuming no mass transfer limitations). The terminal enzyme, hydrogenase, can produce hydrogen (from reduced methyl viologen) at rates of 1.1 moles/hr·mg enzyme. No differences in activity are observed with an atmosphere of (water-scrubbed) producer gas.

Either simultaneously or sequentially with the CO-shift reaction, $H_2$ and $CO_2$ are recombined into new photosynthetic bacterial cell mass in a reaction that is driven by light energy (less than 5% of the irradiated rate is observed in darkness). Radioactive tracer and carbon and redox balances indicate that essentially 100% of the available synthesis gas substrate is converted into cell mass with only an insignificant amount of soluble, extracellular organic materials. Thus, no waste gases have to be separated from the growth chamber and the water is recyclable.

When microbes are confronted by conditions where excess reducing power is available but cell division is inhibited by the absence of an essential nutrient (e.g., a usable form of nitrogen), they conserve that reducing power in the form of osmotically inert, neutral storage materials such as polysaccharides or lipids. Microbial cell mass can be comprised of up to 80 or 90% of these organic storage materials.

A synthesis gas generated by the mechanism of Equation 1 is limiting in the amount of nitrogen available for growth. The bacteria continue to consume CO and $H_2$ in light, but are unable to synthesize protein. They instead recombine CO and $H_2$ according to Equation 5.

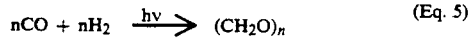

$$nCO + nH_2 \xrightarrow{h\nu} (CH_2O)_n \quad \text{(Eq. 5)}$$

Thus, the overall reaction for synthesis gas conversion by photosynthetic microbes is the sum of Equations 1 and 5, or:

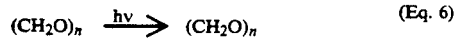

$$(CH_2O)_n \xrightarrow{h\nu} (CH_2O)_n \quad \text{(Eq. 6)}$$

From Equation 6 it is apparent that diverse, heterogeneous organic substrates can be converted into a relatively uniform cell mass product at nearly quantitative efficiencies.

The photosynthetic bacterial strains have been examined for their carbon storage patterns with limiting $N_2$ or $NH_4^+$, which inhibits growth due to a decrease in protein synthesis while promoting the production of organic storage materials. All synthesize both polysaccharide and PHB. Depending on the growth substrate and environmental conditions, however, either one type of storage material or the other is strongly dominant. With exposure to continuous light, ammonia-limited cultures growing on lactic, butyric, or acetic acids synthesize 45% or more of their dry weight as PHB. See Table 1.

With the bacterial strains tested, inhibited photosynthetic growth on synthesis gas resulted primarily in carbohydrate synthesis. Growth inhibition through limiting ammonia yielded a cell mass product containing 34% carbohydrate and 9% bioplastic polymers. Growth could also be inhibited by limiting salts (calcium, magnesium and iron ions) causing the bioplastic polymer to further increase to 27% of cell dry weight. Lesser changes in biopolymer content were observed with limitations in either phosphate, sulfate, trace elements, or vitamins. Altering the medium by the addition of 0.35M NaCl or by raising the medium pH to 10 also caused significant increases in the bioplastic component, regardless of whether synthesis gas or producer gas was the growth substrate.

By far the largest increase in biopolymer content was observed when exogenous acetate was added to the medium in addition to the synthesis gas substrates. Polymer content rose to 79% on average (90% on one occasion).

Another method to enhance the PHB content of photosynthetic bacteria employs their fermentative metabolism. Photosynthetic bacteria ferment sugars in darkness into primarily acetic, butyric, and propionic acids. When subjected to a 12 hour light/12 hour dark cycle of artificial day and night, the synthesis gas components are photoassimilated during the day into endogenous sugars that are then fermented in the night to the organic acid products. If nitrogen is not present, acetic and butyric acids are photoassimilated in the next day cycle into hydroxybutyric acid and propionic acid is photoassimilated into hydroxyvaleric acid. Both are then polymerized into PHB-V. The overall result of day/night cycles is the conversion of an increased portion of the CO and $H_2$ into PHB-V.

Still other methods of increasing the PHB content of photosynthetic bacteria growing on synthetic gas involved establishing intentional co-cultures. Five strains of nonphotosynthetic acetogenic bacteria were isolated that are capable of converting CO into acetate or other organic acids, which are then excreted. The excreted organic acids can then be photoassimilated by photosynthetic bacteria in co-culture to produce plastic biopolymer. The co-cultures are difficult to maintain, however, since the available acetogens are very slow growing and require high levels of ammonium ion as an essential nutrient. Biopolymers averaged about 4% of cell dry weight.

The fermentative breakdown of newly-synthesized endogenous polysaccharides of photosynthetic bacteria to the level of acetate and other organic acids is stimulated by the presence of trace amounts of oxygen. Algae produce oxygen in light. Establishing co-cultures of algae and photosynthetic bacteria in the presence of synthesis gas yielded a product of about 18% bioplastic polymer. See Table 1. Algal numbers in the mixed population are easily controlled by their relatively slow growth and by limiting ammonia (they do not utilize $N_2$).

PHB and copolymers can be readily isolated from bacteria after extraction of cells with 5% sodium hypochlorite for one hour followed by removal of other lipids by acetone and ethanol solubilization. PHB is then dissolved in warm chloroform. The bioplastic polymer synthesized by photosynthetic bacteria under these conditions was analyzed by nuclear magnetic resonance. The polymers were comprised of about 70% hydroxybutyric acid and 30% hydroxyvaleric acid. A 70/30 PHB-V polymer exhibits physical properties similar to polyethylene.

There are several reasons why it is believed not to be necessary to operate the process under sterile conditions. Carbon monoxide is toxic to most living things, including most potential pathogens. If necessary, however, the process can be easily adapted to sterile conditions since the gasification step sterilizes the gaseous substrates.

Figure 2:
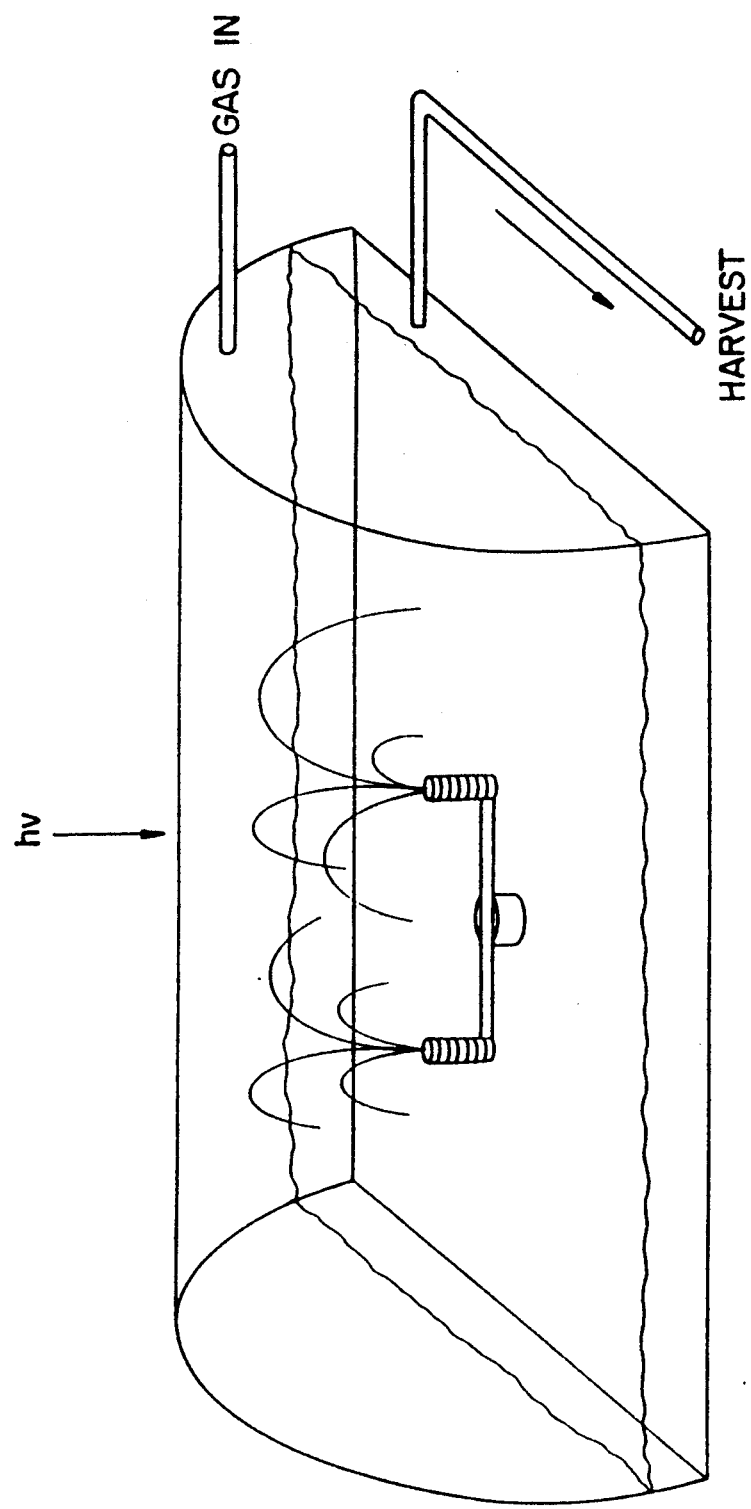
FIG. 2 illustrates another embodiment of a reactor which is useful in this invention.

FIGS. 1 and 2 illustrate two types of useful reactors which may be used in practicing the techniques of this invention. A continuous-flow bubble tower design is shown in FIG. 1 in which the gaseous substrates are pumped from the head space to a sparging system at the base of the water column containing photosynthetic bacterial suspensions. Make-up gas was provided as needed. Bacteria were harvested and fresh mineral medium was supplied continuously. Water recycle was not attempted although the absence of organic waste materials indicates its feasibility. Initial growth was luxuriant, but the high concentrations of ammonium ion in the medium allowed the development of a contaminating sulfate-reducing bacterium. A shift to low ammonium ion or limiting $N_2$ prevented the growth of the contaminating bacterium. Other trace mineral nutrients (1) can be leached from the gasifier ash by the bacteria in the aqueous medium, or (2) can be added separately to the aqueous medium. The reactor is transparent to solar energy. The harvest crop of bacterial cell mass is withdrawn from one end of the reactor.

A second reactor design is shown in FIG. 2 in which a submersible pump is used to spray a photosynthetic bacterial liquid suspension into a $H_2$ and CO gas phase in order to effect mass transfer by increasing the contact surface area. Pumping did not cause any damage to the microbial cells. Growth of the photosynthetic bacteria on $H_2$ and CO in sunlight was heavy.

Figure 3:
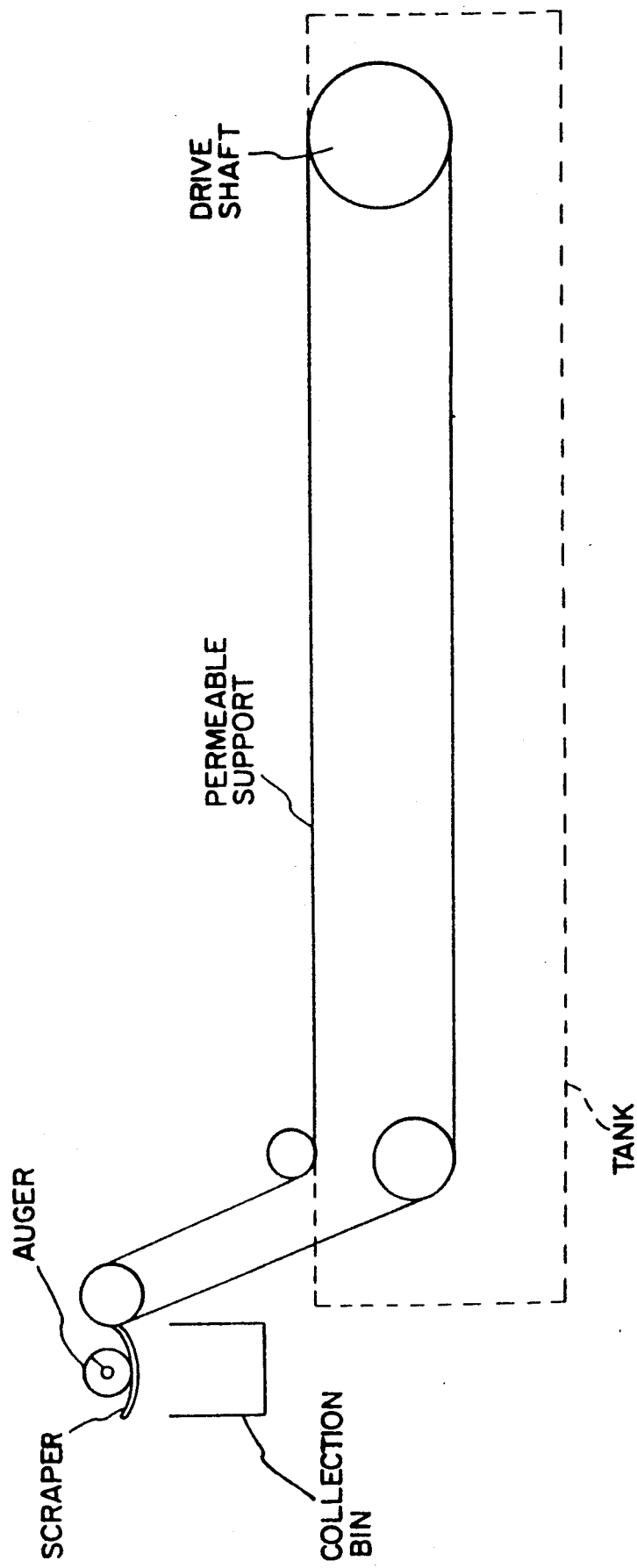
FIG. 3 is a schematic diagram illustrating another embodiment of apparatus which is useful for producing bioplastic polymer.

Another alternative is to innoculate the photosynthetic bacteria on the upper surface of a permeable support (e.g., canvas or low density plastic film with pinholes) which floats on the surface of a liquid medium. This is illustrated in the diagram of FIG. 3. The permeable support is shown as a flexible endless belt which extends around various rollers. The upper portion of the belt is positioned at the surface of the liquid medium in the tank.

In this arrangement the bacteria has maximal exposure to the gasified biomass atmosphere (carbon monoxide and hydrogen) and to solar energy from above, while receiving water and mineral nutrients from the liquid medium (e.g., through a wicking action). The bacterial cell mass develops as a thick paste on the permeable support surface. The bioplastic polymer is scraped off the belt and augered into a collection bin. No pumping is required.

The process of this invention utilizes carbon monoxide as the sole source of carbon, i.e., there is no need to add any yeast extract or other complex organic substrates. The organic starting materials, regardless of type, are first thermally converted to synthesis gas which is then fed to illuminated photosynthetic bacteria. This distinguishes the present process from previously known techniques.

The foregoing is considered as illustrative only of the principles of the invention. Further, because numerous modifications and changes will readily occur to those skilled in the art, it is not desired to limit the invention to the exact construction and operation shown and described, and accordingly all suitable modifications and equivalents may be resorted to falling within the scope of the invention as redefined by the claims which follow.

TABLE 1

Photosynthesis of Storage Polymers (Rhodobacter sp. CBS)

| Growth Condition | Growth Substrate | Carbohydrate (% dry wt.) | PHB (% dry wt.) |
| --- | --- | --- | --- |
| Complete medium | lactate | 32 | 7 |
| Limiting $NH_4^+$ | lactate | 24 | 45 |
| $-NH_4^+$, $+N_2$ | lactate | 27 | 41 |
| Limiting $NH_4^+$ | acetate | 11 | 50 |
| Complete medium | $H_2 + CO$ | 12 | <1 |
| Limiting $NH_4^+$ | $H_2 + CO$ | 34 | 9 |
| $-NH_4^+$, $+N_2$ | $H_2 + CO$ | 27 | 3 |
| $-NH_4^+$, $-$salts, $+N_2$ | $H_2 + CO$ | 26 | 27 |
| $-NH_4$, limiting $N_2$ | $H_2 + CO + $ acetate | 8 | 79 |
| $-NH_4^+$, $+N_2$, pH 10 | $H_2 + CO$ | 40 | 32 |
| $-NH_4^+$, $+N_2 + $ 0.35M NaCl | $H_2 + CO$ | 61 | 17 |
| $-NH_4^+$, $+N_2$, 12 hr light | $H_2 + CO$ | 25 | 14 |
| Limiting $NH_4^+$, $+$ alga | $H_2 + CO$ | 16 | 18 |

The embodiments of the invention in which an exclusive property or privilege is claimed are defined as follows:

1. A process for producing cell mass, comprising the steps of:
    (a) thermally gasifying organic materials to produce a gaseous mixture consisting essentially of carbon monoxide and hydrogen;
    (b) contacting said mixture with photosynthetic bacteria selected from the group consisting of the Rhodospirillales order of photographic bacteria; wherein said bacteria metabolizing carbon monoxide in light; and
    (c) exposing said bacteria to radiant energy whereby said gaseous mixture is assimilated by said bacteria into bacterial cell mass.

2. A process in accordance with claim 1, wherein said gaseous mixture is contacted by said bacteria under anaerobic conditions.

3. A process in accordance with claim 1, wherein said organic materials comprise biomass material.

4. A process in accordance with claim 1, wherein said radiant energy comprises solar energy.

5. A process in accordance with claim 4, wherein said gaseous mixture is exposed to said bacteria in a reactor into which solar energy is permitted to enter.

6. A process in accordance with claim 1, wherein said organic materials are thermally combusted.

7. A process in accordance with claim 1, wherein said photosynthetic bacteria is selected from the group consisting of *Rhodocyclus gelatinosus*, *Rhodoseudomonas palustris*, *Rhodospirillum molischianum*, and *Rhodopseudomonas capsulata*.

8. A process in accordance with claim 1, wherein said bacteria are present in an aqueous medium.

* * * * *